United States Patent
Ulmsten et al.

(10) Patent No.: US 7,087,065 B2
(45) Date of Patent: Aug. 8, 2006

(54) MESH FOR PELVIC FLOOR REPAIR

(75) Inventors: Ulf Ulmsten, Danderyd (SE); Barbara Schwartz, Morganville, NJ (US); Rebecca Leibowitz, Summit, NJ (US)

(73) Assignee: Ethicon, Inc., Somerville, NJ (US)

( * ) Notice: Subject to any disclaimer, the term of this patent is extended or adjusted under 35 U.S.C. 154(b) by 315 days.

(21) Appl. No.: 10/263,933

(22) Filed: Oct. 3, 2002

(65) Prior Publication Data

US 2003/0114866 A1    Jun. 19, 2003

Related U.S. Application Data

(60) Provisional application No. 60/327,160, filed on Oct. 4, 2001.

(51) Int. Cl.
*A61B 17/04* (2006.01)
*A61F 13/00* (2006.01)

(52) U.S. Cl. .......................... 606/151; 600/37
(58) Field of Classification Search ................. 606/151; 601/37; 600/37; 128/898
See application file for complete search history.

(56) References Cited

U.S. PATENT DOCUMENTS

| | | |
|---|---|---|
| 3,182,662 A | 5/1965 | Shirodkar |
| 3,212,502 A | 10/1965 | Myers |
| 3,311,110 A | 3/1967 | Singman |
| 3,372,695 A | 3/1968 | Beliveau et al. |
| 3,472,232 A | 10/1969 | Earl |
| 3,608,095 A | 9/1971 | Barry |
| 3,763,860 A | 10/1973 | Clarke |
| 3,858,783 A | 1/1975 | Kapitanov et al. |
| 3,924,633 A | 12/1975 | Cook et al. |
| 4,037,603 A | 7/1977 | Wendorff |
| 4,128,100 A | 12/1978 | Wendorff |
| 4,235,238 A | 11/1980 | Ogiu et al. |
| 4,392,495 A | 7/1983 | Bayers |
| 4,441,497 A | 4/1984 | Paudler |
| 4,509,516 A | 4/1985 | Richmond |
| 4,549,545 A | 10/1985 | Levy |

(Continued)

FOREIGN PATENT DOCUMENTS

AU    278089 B    6/1965

(Continued)

OTHER PUBLICATIONS

PCT Written Opinion, dated Dec. 18, 2003, for PCT Appl. No. PCT/US02/31681.

(Continued)

*Primary Examiner*—Gary Jackson

(57) ABSTRACT

A woven mesh is provided for supporting tissue or an organ within a female patient's pelvis, and a method for using the same. The mesh includes a central portion having a width, a length, first and second ends, and first and second side edges, and first and second wing portions extending from the first and second ends of the central portion respectively. The first and second wing portions each have a width, a length, and first and second peripheral edges. The width of the wing portions are each greater than the width of the central portion, and when positioned within the female patient, the central portion is positioned below and supports the tissue or organ. A mesh is also provided having woven fibers with voids therebetween, and having a central portion and first and second ends. The average size of the voids at least in the central portion is at least 25–50 mm$^2$, and when positioned within the patient, the central portion is positioned below and supports the tissue or organ.

4 Claims, 2 Drawing Sheets

U.S. PATENT DOCUMENTS

| | | | |
|---|---|---|---|
| 4,633,873 A * | 1/1987 | Dumican et al. ............ 606/151 |
| 4,655,221 A * | 4/1987 | Devereux ................... 606/151 |
| 4,946,467 A | 8/1990 | Ohi et al. |
| 5,013,292 A | 5/1991 | Lemay |
| 5,032,508 A | 7/1991 | Naughton et al. |
| 5,080,667 A | 1/1992 | Chen et al. |
| 5,112,344 A | 5/1992 | Petros |
| 5,180,385 A | 1/1993 | Sontag |
| 5,250,033 A | 10/1993 | Evans et al. |
| 5,281,208 A * | 1/1994 | Thompson et al. ......... 604/378 |
| 5,281,237 A | 1/1994 | Gimpelson |
| 5,337,736 A | 8/1994 | Reddy |
| 5,362,294 A | 11/1994 | Seitzinger |
| 5,368,595 A | 11/1994 | Lewis |
| 5,368,756 A | 11/1994 | Vogel et al. |
| 5,382,257 A | 1/1995 | Lewis et al. |
| 5,383,904 A | 1/1995 | Totakura et al. |
| 5,403,328 A | 4/1995 | Shallman |
| 5,429,626 A * | 7/1995 | Fenton ....................... 604/339 |
| 5,450,860 A | 9/1995 | O'Connor |
| 5,480,436 A | 1/1996 | Bakker et al. |
| 5,507,796 A | 4/1996 | Hasson |
| 5,549,589 A * | 8/1996 | Horney et al. .............. 604/366 |
| 5,582,188 A | 12/1996 | Benderev |
| 5,611,515 A | 3/1997 | Benderev et al. |
| 5,628,756 A | 5/1997 | Barker, Jr. et al. |
| 5,645,568 A | 7/1997 | Chervitz et al. |
| 5,741,299 A | 4/1998 | Rudt |
| 5,816,258 A | 10/1998 | Jervis |
| 5,836,315 A | 11/1998 | Benderev et al. |
| 5,840,011 A | 11/1998 | Landgrebe et al. |
| 5,855,549 A | 1/1999 | Newman |
| 5,860,425 A | 1/1999 | Benderev et al. |
| 5,899,909 A | 5/1999 | Claren et al. |
| 5,899,999 A | 5/1999 | De Bonet |
| 5,922,026 A | 7/1999 | Chin |
| 5,934,283 A | 8/1999 | Willem et al. |
| 5,935,122 A | 8/1999 | Fourkas et al. |
| 5,945,122 A | 8/1999 | Abra et al. |
| 5,997,554 A | 12/1999 | Thompson |
| 6,030,393 A | 2/2000 | Corlew |
| 6,042,534 A | 3/2000 | Gellman et al. |
| 6,110,101 A | 8/2000 | Tihon et al. |
| 6,117,067 A | 9/2000 | Gil-Vernet |
| 6,197,036 B1 | 3/2001 | Tripp et al. |
| 6,221,005 B1 | 4/2001 | Bruckner et al. |
| 6,273,852 B1 * | 8/2001 | Lehe et al. ..................... 600/30 |
| 6,306,079 B1 * | 10/2001 | Trabucco ...................... 600/30 |
| 6,315,765 B1 * | 11/2001 | Datta et al. ............ 604/385.24 |
| 6,334,446 B1 | 1/2002 | Beyar |
| 6,382,214 B1 | 5/2002 | Raz et al. |
| 6,406,423 B1 * | 6/2002 | Scetbon ........................ 600/30 |
| 6,475,139 B1 | 11/2002 | Miller |
| 6,491,703 B1 | 12/2002 | Ulmsten |
| 6,605,097 B1 | 8/2003 | Lehe et al. |
| 6,755,781 B1 * | 6/2004 | Gellman ....................... 600/38 |
| 2001/0018549 A1 | 8/2001 | Scetbon |
| 2001/0049467 A1 | 12/2001 | Lehe et al. |
| 2002/0028980 A1 | 3/2002 | Thierfelder et al. |
| 2002/0058959 A1 | 5/2002 | Gellman |
| 2002/0077526 A1 | 6/2002 | Kammerer et al. |
| 2002/0091373 A1 | 7/2002 | Berger |
| 2002/0188169 A1 | 12/2002 | Kammerer et al. |
| 2003/0023138 A1 | 1/2003 | Luscombe |
| 2003/0100954 A1 | 5/2003 | Schuldt-Hempe |
| 2003/0149440 A1 | 8/2003 | Kammerer et al. |
| 2003/0176762 A1 | 9/2003 | Kammerer et al. |

FOREIGN PATENT DOCUMENTS

| | | |
|---|---|---|
| AU | 441561 B | 1/1972 |
| DE | 4334419 A1 | 4/1995 |
| EP | 0598976 A2 | 6/1994 |
| EP | 0941712 A1 | 9/1999 |
| EP | 1025811 A2 | 8/2000 |
| SE | 503271 | 4/1996 |
| WO | WO 9003766 A1 | 4/1990 |
| WO | WO 9606567 A1 | 3/1996 |
| WO | WO 9713465 A1 | 4/1997 |
| WO | WO 9831301 A1 | 7/1998 |
| WO | WO 01/39870 A1 | 6/2001 |
| WO | WO 0219944 A2 | 3/2002 |
| WO | WO 0238079 A2 | 5/2002 |
| WO | WO 02078567 A1 | 10/2002 |

OTHER PUBLICATIONS

Petros, P.E. Papa, "Vault Prolapse II: Restoration of Dynamic Vaginal Supports by Infracoccygeal Sacropexy, an Axial Day-Case Vaginal Procedure". International Urogynecol Journal, Springer-Verlag London Ltd., 2001, vol. 12, p. 263-303.

Petros, P.E. Papa, "Vault Prolapse 1: Dynamic Supports of the Vagina", International Urogynecol Journal, Springer-Verlag London Ltd., 2001, vol. 12, pp. 292-295.

Petros, P.E. Papa, "An Integral Theory for the Diagnosis and Management of Female Urinary Incontinence", Scandinavian Journal of Urology and Nephrology, Supplement 153: 1993.

"TVT Tension-Free Vaginal Tape, Minimally Invasive Highly Effective Treatment for Female Stress Urinary Incontinence", Gynecare, Ethicon, Inc., 1999, pp. 1-6.

U.S. Patent Application "Mesh Tape With Wing-Like Extensions For Treating Female Urinary Incontinence", U.S. Appl. No. 10/854,289, filed May 7, 2004.

* cited by examiner

MESH FOR PELVIC FLOOR REPAIR

CROSS-REFERENCE TO RELATED APPLICATION

The present invention claims the benefit of earlier-filed U.S. provisional patent application Ser. No. 60/327,160, filed on Oct. 4, 2001.

FIELD OF THE INVENTION

The present invention relates generally medical devices used for pelvic floor repair. More particularly, the invention is directed to mesh designs having particular application for pelvic floor repair, including vaginal and rectal prolapse repair.

BACKGROUND OF THE INVENTION

Synthetic mesh implant materials are often needed to buttress the repair of vaginal prolapse (e.g. cystocele, rectocele, enterocele). Following an anterior colporrhaphy repair, flat sheets of knitted synthetic mesh are used to replace the structural support function of the endopelvic fascia, connective tissue between the anterior wall of the vagina and bladder. However, clinicians are reluctant to use currently available mesh implants because of observed mesh-related complications such as erosion and infection of surrounding tissue, which can lead to recurrence of prolapse or the need to remove the mesh. These complications are often due to a mesh construction that is too bulky, too stiff, or too dense for the delicate vaginal tissue area.

There are no known synthetic meshes with attributes that adequately address these problems and the specific needs of pelvic floor repair. To avoid the risks associated with currently available synthetic knitted meshes, some clinicians have chosen to use biologic materials such as sheets of processed cadaveric fascia lata or dermal tissue or patches composed of animal-derived tissue. However, these materials pose risks such as disease transmission, and supply and quality control, and are prohibitively expensive. Further, these materials typically are not uniform in composition, which can lead to tearing or other problems when surgically placing the devices or following implantation.

SUMMARY OF THE INVENTION

The current invention is a mesh that is specially designed for use in the pelvic floor region, such as to reduce vaginal prolapse and reinforce weakened tissues in this area following a surgical repair. The unique shape and construction of the mesh is designed to minimize the amount of foreign body material implanted in the pelvic floor tissues in order to reduce the risk of erosion, infection, and rejection. The construction of the current invention minimizes the amount of material by incorporating a larger void size in at least the area that contacts or supports the target tissue or organ, and/or providing a mesh shaped so that less material is present in this area. The mesh may have either denser voids and/or a larger size in the region of the lateral edges to support adequate mechanical fixation.

In one embodiment of the present invention, a mesh is provided for use in supporting tissue or an organ within a female patient's pelvis. The mesh includes a central portion having a width, a length, and first and second side edges, and first and second wing portions extending from the first and second side edges of the central portion. The first and second wing portions each have a width, a length, first and second ends, and first and second peripheral edges. The width of the first and second wing portions is each greater than the width of the central portion. Further, when implanted in the female patient, the central portion of the mesh is positioned below and supports the tissue or organ. In another embodiment, the first and second peripheral edges of the first and second wing portions extend outwardly at an obtuse angle from the first and second side edges of the central portion respectively, and in yet another embodiment, the mesh has a butterfly configuration.

In another embodiment, the width of the central portion is at least 5 cm, the width of the first and second wing portions are at least 9 cm, the length of the central portion is at least 6 cm, and/or the length of the first and second wing portions are at least 1.5 cm.

In alternate embodiments, the mesh may be further comprised of a synthetic material, or a combination of synthetic and natural materials.

In yet another embodiment, the mesh further includes a plurality of woven synthetic fibers having voids therebetween that have an average void size of at least about 25–50 $mm^2$, and in yet another embodiment the mesh further includes a plurality of woven synthetic fibers having voids therebetween that have an average void size that is larger in the central portion than in the wing portions.

In an alternate embodiment, the voids in the central portion have an average void size of at least about 25–50 $mm^2$, and the voids in the wing portions have an average void size less than that of the central portion. In yet another embodiment, the voids progressively increase in size from the outer edge of the wing portions to a central region of the central portion.

Also provided is a device for use in supporting tissue or an organ within a female patient's pelvis. The device includes a mesh of woven fibers having voids therebetween, and having a central portion and first and second ends. The voids in at least said central portion have an average size of at least about 25–50 $mm^2$, and the mesh is sized and shaped so that, when inserted within a female patient, the central portion is positioned below and supports the tissue or organ.

A method is also provided for supporting a prolapsed organ within a female patient's pelvis. The method includes the steps of providing a mesh of woven fibers having voids therebetween and having a central portion and first and second ends. The voids in at least the central portion have an average void size of at least about 25–50 $mm^2$. The method further includes the step of inserting the mesh into the female patient so that the central portion is positioned below and supports the tissue or organ.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Figure 2:
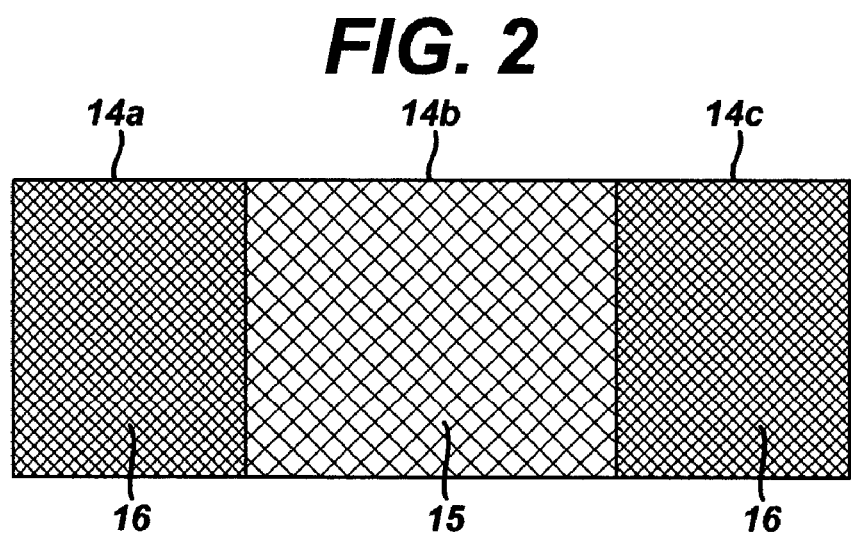
FIG. 2 illustrates a mesh according to the present invention including a portion having increased voids.
Figure 4:
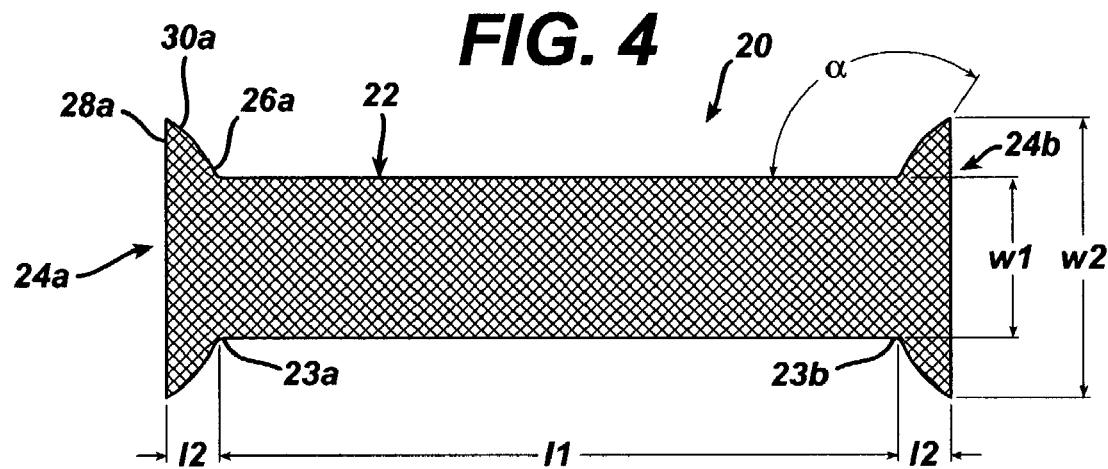
FIG. 4 illustrates an alternate mesh design according to the present disclosure.
Figure 5:
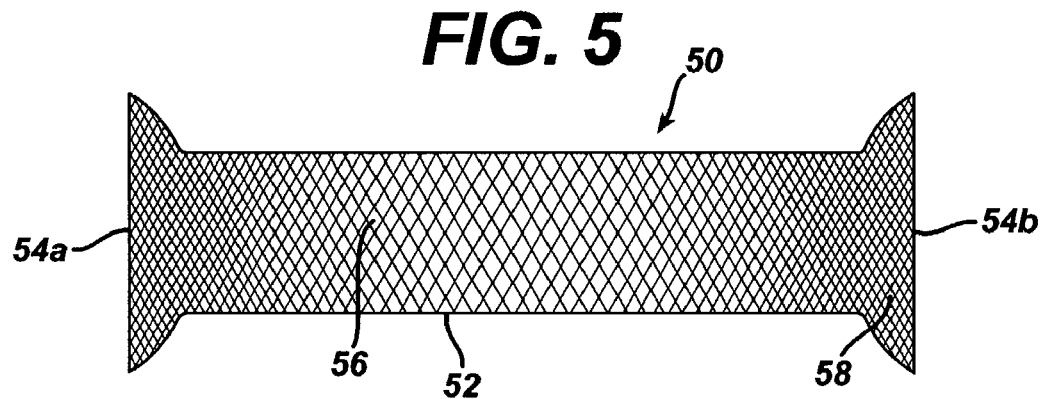
FIG. 5 illustrates another mesh design according to the present disclosure.

FIGS. 2, 4 and 5 illustrate generally various mesh configurations and designs according to the present invention having particular application for pelvic floor repair, and in particular, for repair of vaginal, rectal, or other prolapses. Although particular designs are illustrated and described, those skilled in the art will recognize that other configurations are also possible without departing from the spirit and scope of the invention described herein. The present invention is to be limited only by the claims set forth herein.

The current invention is a woven mesh, which is specially designed for use in the pelvic floor region for applications such as reducing vaginal prolapse and/or reinforcing weakened tissues in this area following a surgical repair. The unique shape and construction of the mesh is designed to minimize the amount of foreign body material implanted in the pelvic floor tissues, to thereby reduce the risk of erosion, infection, and rejection.

Figure 1:
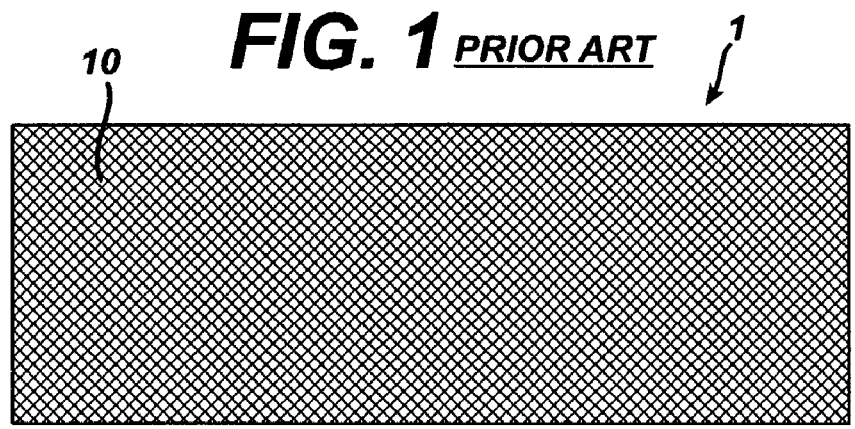
FIG. 1 illustrates a prior art mesh design.
Figure 3:
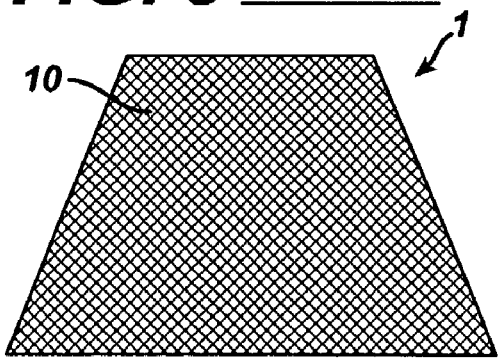
FIG. 3 illustrates a prior art trapezoidal mesh design.

Common prior art mesh designs are illustrated in FIGS. 1 and 3. As shown, these meshes 1 are substantially rectangular or trapezoidal in shape, and have a pore or void 10 sizes in the order of approximately 0.2 $mm^2$ to 2.4 $mm^2$. Meshes having this shape and pore size do not adequately address the needs particular to pelvic floor repair. As stated above, tissue supported by the mesh in pelvic floor repair, such as vaginal tissue, is sensitive tissue, and may become irritated by contact with these denser meshes.

The above-described problems can be reduced or eliminated by providing a mesh having less density at least in the region of sensitive tissue, such as vaginal tissue. Adequate strength is provided at the fixation sites by providing portions of the mesh having increased density, and/or by providing a mesh having a larger area for fixation at these sites. According to one embodiment of the present invention illustrated in FIG. 2, the mesh 13 may consist of three portions 14a, 14b, 14c. The two end portions 14a, 14c may have a void size 16 in the order of that shown known in the prior art (i.e., Prolene® soft mesh having a pore size of approximately 2.38 $mm^2$), with the middle or central portion 14c being comprised of the same mesh material, but having an increased void size 15 of at least 25–50 $mm^2$. With pelvic floor repair, the end portions of the mesh are typically secured to less sensitive tissue than vaginal tissue, for example the tendonous arch or the connective tissue attached to the vaginal epithelium in the case of vaginal prolapse repair. Thus, the embodiment illustrated in FIG. 2 provides denser material having smaller void sizes to be used at the fixation sites, and less dense material having larger void sizes in the area that is in contact with or otherwise supporting the vaginal tissue or other organ.

In an alternate embodiment, the problems associated with prior art meshes set forth above can be improved by different mesh configurations that reduce the mesh area in contact with the sensitive tissue or organ. According to one embodiment shown in FIG. 4, a mesh 20 is provided having a "butterfly" shape configuration. The mesh 20 has a thinner central portion 22, and two wing portions 24a, 24b extending outwardly from first and second ends 23a, 23b of the central portion 22.

Figure 6:
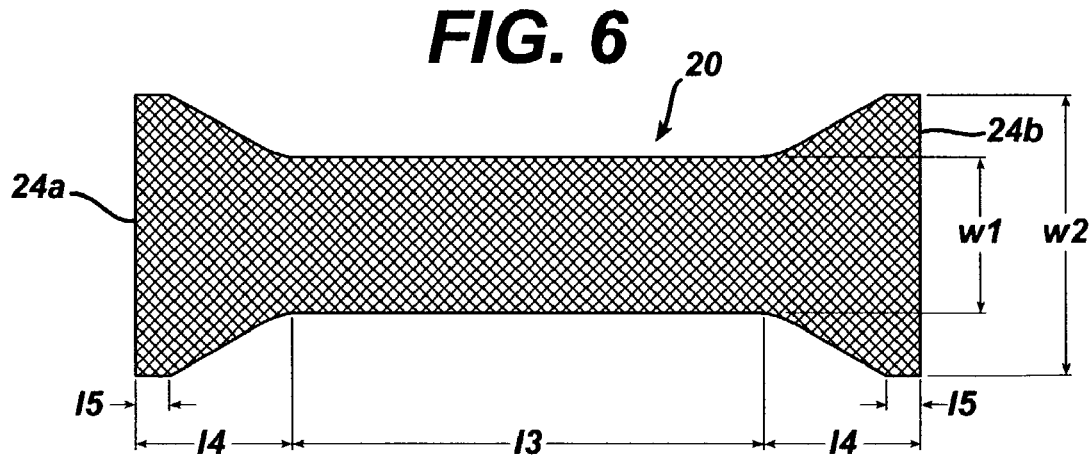
FIG. 6 illustrates yet another mesh design according to the present disclosure.

The wing portions have a width w2 greater than the width w1 of the central portion. In a preferred embodiment these widths are approximately 9–10 cm and 4.5–5.5 cm respectively, and the lengths l1, l2 of the central portion and wings respectively are approximately 12 cm and 1.5 cm. In an alternate "butterfly" configuration illustrated in FIG. 6, the dimensions 13, 14,15 are preferably 6.4 cm, 4.8 cm, and 1 cm respectively. The wing portions may also increase in width from an inner side of the wing 26a to the outer edge of the wing 28a. In one embodiment peripheral edges 30a of the wing portion extend from the inner side 26a to the outer edge 28a is at an angle α of about 145–150 degrees relative to the side edges 28 of the central portion.

In yet another embodiment shown in FIG. 5, the mesh may incorporate a combination of the features described above. Mesh 50 has a similar butterfly configuration as the mesh described above, including a central portion 52 and two wing portions 54a, 54b at each end. This embodiment, however, further includes larger voids 56 in the central portion than the voids 58 in the wing portions. In one embodiment, the voids are approximately 25–50 $mm^2$ wide in the central portion, and approximately 1 $mm^2$ in the wing portions. In a preferred embodiment, the voids are approximately 25–50 $mm^2$ in the central portion and gradually decrease in size to approximately 1 $mm^2$ at the distal edge of the wing portions.

Meshes according to the present invention may consist of a composite of different fibers, one of which may be a partially absorbable material such as VYPRO®, which is a mesh material manufactured by Ethicon, Inc. of Somerville, N.J. This material is approved by the F.D.A. for implant into the human body. In other embodiments, suitable non-absorbable fibers include Prolene®, Pronova® or PDS®, all also manufactured by Ethicon, Inc. of Somerville, N.J. Other embodiments may also incorporate proliferation-stimulating agents, such as fibroblast growth factor (FGF) or transforming growth factor (TGFβ), into the wing portions to stimulate growth from the lateral edges of the pelvic side wall into these portions of the mesh. Alternatively, glue or other adhesives may be incorporated to affix the mesh in these areas. Preferably, the mesh would be provided to the doctor in the pre-cut butterfly shape, eliminating the decision of how to orient the mesh in the pelvic floor area during an anterior vaginal wall repair.

Thus, each of the meshes described above reduce the amount of material present in the central portion of the mesh, thereby minimizing or avoiding the risk of erosion in particularly sensitive areas, while still allowing for enough material to securely fix the mesh to lateral attachment sites.

Although exemplary embodiments and methods for use have been described in detail above, those skilled in the art will understand that many variations are possible without departing from the spirit and scope of the invention, which is limited only by the appended claims.

What is claimed is:

1. A mesh for use in supporting tissue or an organ within a female patient's pelvis comprising:
   a central portion having a width, a length, first and second ends, and first and second side edges; and
   first and second wing portions extending from the first and second ends of the central portion, the first and second wing portions each having a width, a length, first and second ends, and first and second peripheral edges,
   wherein the width of the first and second wing portions are each greater than the width of the central portion and wherein, when implanted in the female patient, the central portion is positioned beneath and supports the tissue or organ, and
   wherein the mesh further comprises a plurality of woven synthetic fibers having voids therebetween, and wherein the voids are larger in size in the central portion than in the wing portions.

2. The mesh according to claim 1, wherein the voids in the central portion have an average size of at least about 25–50 mm$^2$, and wherein the voids in the wing portions have an average size of less than about 3 mm$^2$.

3. The mesh according to claim 1, wherein the voids progressively increase in size from the outer edge of the wing portions to a central region of the central portion.

4. A method for supporting tissue or an organ within a female patient's pelvis, comprising:

providing a mesh having a central portion having a width, a length, first and second ends, and first and second side edges, and having first and second wing portions extending from the first and second ends of the central portion, the first and second wing portions each having a width, a length, first and second ends, and first and second peripheral edges, wherein the width of the first and second wing portions are each greater than the width of the central portion;

inserting the mesh into the female patient so that substantially only the central portion is in contact with vaginal tissue, and so that the wing portions are fixated to non-vaginal tissue to thereby provide support for the vaginal tissue.

* * * * *